United States Patent [19]

Fields

[11] 4,347,384

[45] Aug. 31, 1982

[54] PRODUCTION OF MERCAPTANS

[75] Inventor: Ellis K. Fields, River Forest, Ill.

[73] Assignee: Standard Oil Company (Indiana), Chicago, Ill.

[21] Appl. No.: 246,669

[22] Filed: Mar. 23, 1981

[51] Int. Cl.$^3$ .................. B01J 31/02; B01J 27/02; C07C 149/06; C07C 143/16
[52] U.S. Cl. ........................ 568/37; 568/72; 252/426; 252/436; 260/513 R
[58] Field of Search ............ 568/72, 37; 252/426, 252/436; 260/513 R

[56] References Cited

U.S. PATENT DOCUMENTS 2,615,786  10/1952  Proell et al. ................. 568/72

*Primary Examiner*—Henry R. Jiles
*Assistant Examiner*—Robert C. Whittenbaugh
*Attorney, Agent, or Firm*—Gunar J. Blumberg; William T. McClain; William H. Magidson

[57] ABSTRACT

Trifluoromethylsulfonic acid has been found to be an extremely useful catalyst for the manufacture of mercaptans from olefins or viscous polyolefins and hydrogen sulfide. Also a novel process for the preparation of mercaptans is disclosed which proven comprises reacting olefins or polyolefins at a temperature of about −10° to 70° C. with hydrogen sulfide under pressure of about 1 to 10 atmospheres in the presence of about 0.05 to 10 percent by weight of the olefins of the trifluoromethylsulfonic acid. The mercaptans produced according to the novel process are useful in the preparation of nonionic surfactants for lubricating oils and in the enhanced oil recovery as well as for biocides. Novel beta-polybutenylsulfoxy-alpha-hydroxyethylbenzenes have also been prepared. These are useful in the preparation of nonionic surfactants for lubricating oils and as biocides.

4 Claims, No Drawings

PRODUCTION OF MERCAPTANS

BACKGROUND OF THE INVENTION

Field of the Invention

This invention relates to the production of mercaptans from olefins, viscous polyolefins and hydrogen sulfide utilizing trifluoromethylsulfonic acid as a catalyst.

It is an object of this invention to provide trifluoromethylsulfonic acid as a catalyst for the manufacture of mercaptans from olefins and viscous polyolefins and hydrogen sulfide and novel beta-polybutenylsulfoxy-alpha-hydroxyethylbenzenes. It is a further object to provide a process for the manufacture of mercaptans which process comprises reacting olefins or polyolefins with hydrogen sulfide in the presence of trifluoromethylsulfonic acid. Further objects and advantages will become apparent as the description of the invention proceeds including the object of providing mercaptans useful in the preparation of nonionic surfactants for lubricating oils and in enhanced oil recovery, as well as for biocides.

One route to the preparation of mercaptans has been the reaction of a primary alkyl halide with sodium hydrosulfide to form the corresponding alkyl mercaptans and sodium chloride. Another prior art method is the reaction of an alcohol with hydrogen sulfide over thoria to obtain the corresponding mercaptans plus water. In U.S. Pat. No. 3,045,053 (1962) a process for reacting olefinically unsaturated compounds with hydrogen sulfide is disclosed. That process comprises carrying out the reaction in the conjoint presence of an organic peroxide and at least one finally divided elemental metal in Group VIII of the Fourth Period of the Periodic Table. U.S. Pat. No. 2,031,601 (1950) discloses the preparation of mercaptans from polymeric olefins utilizing anhydrous aluminum chloride and related Friedel Crafts catalysts.

I have discovered that trifluoromethylsulfonic acid is a very effective catalyst for the manufacture of mercaptans from olefins and viscous polyolefins and hydrogen sulfide. A unique feature of this catalyst is that in the olefinic reactions it catalyzes both polymerization and hydrogen sulfide addition in one reaction. When diisobutylene is a reactant along with hydrogen sulfide, mercaptans of molecular weight higher than tertiary octyl mercaptans are produced.

I have discovered a process for the preparation of mercaptans which comprises reacting olefins or polyolefins at a temperature of about 10° to 70° C. with hydrogen sulfide under pressure of about 1 to 10 atmospheres in the presence of about 0.05 to 10 percent by weight of the olefins of trifluoromethylsulfonic acid. My preferred temperature range is 10° to 35° C. and the preferred pressure range is 1 to 5 atmospheres. The mercaptans produced according to my novel process are useful in the preparation of nonionic surfactants for lubricating oils and in enhanced oil recovery as well as for biocides.

A wide variety of olefinically unsaturated organic compounds may be reacted with hydrogen sulfide in accordance with my invention. Suitable charge stocks comprise a wide variety of olefinically unsaturated organic compounds. These may be reacted with hydrogen sulfide in accordance with the invention. Suitable charge stocks comprise ethylene, propylene, butene-1, butene-2, isobutylene, pentene-1, heptene-1, octene-1, dodecene-1, tetradecene-1, or their mixtures, or other alkenyl hydrocarbons. Examples of isoalkenyl compounds suitable for use herewith include 3-methyl butene, 4-methyl pentene, dimethyl hexene, or their mixtures with each other. Aryl olefins may also be used, and are exemplified by styrene, alpha-methyl styrene, etc. Suitable diolefins, which may be reacted to form dimercaptans and olefinically unsaturated mercaptans, include butadiene, piperylene, isoprene, etc., or their admixtures with alkenes; cyclic olefins, such as cyclopentene, methyl cyclopentenes, cyclopentadienes, dicyclopentadienes, etc.; my preferred olefins are diisobutylene and polybutene. My novel catalyst trifluoromethylsulfonic acid is useful in converting all of the aforementioned olefins with hydrogen sulfide to the appropriate mercaptans. These mercaptans are particularly useful in the preparation of surfactants for lubricating oils and as biocides. I have also discovered as novel composition of matter beta-polybutenylsulfoxy-alpha-hydroxyethylbenzenes and mercaptans of the following formula

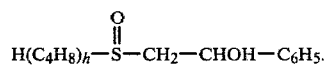

Usually h=8 but h can have a value from 6 to 10.

The following examples illustrate the preferred embodiment of this invention. It will be understood that these examples are for illustrative purposes only and do not purport to be wholly definitive with respect to conditions or scope of the invention.

EXAMPLE 1

A mixture of 87.8 ml (0.05 mole) of commercial diisobutylene (80% 2,2,4-trimethylpentene-1 and 20% 2,4,4-trimethylpentene-2) and 1 ml of trifluoromethylsulfonic acid was shaken in a Parr apparatus under 26 psig hydrogen sulfide at 25° C. for 2 hours. The mixture was washed with water to remove the catalyst, dried, and distilled, giving these fractions:

Fraction 1. 126°–152° C. at 200 torr, 18.7 g.
Fraction 2. 160°–210° C. at 200 torr, 25.7 g.
Fraction 3. 215°–230° C. at 200 torr, 5.7 g.
Analysis. Fr. 1. C, 74.0; H, 13.7, S, 10.6; mercaptan S, 10.3; Fr. 2. C, 79.4; H, 13.9; S, 6.3; mercaptan S, 6.2; Fr. 3. C, 79.6; H, 12.3; S, 8.1; mercaptan S, 4.0.

Fraction 1 analyzes moderately well for a mercaptan of a dimer of diisobutylene, $C_{16}H_{33}SH$; C, 74.4; H, 13.2; S, 12.4.

Fraction 2 analyzes approximately for a mercaptan of diisobutylene tetramer, $C_{32}H_{65}SH$; C, 79.4; H, 13.7; S, 6.6.

EXAMPLE 2

A mixture of 70.2 g (0.2 mole) of L-14 polybutene, mole wt. 351, 50 ml of n-pentane, and 1 ml of trifluoromethylsulfonic acid was shaken under 25 psig hydrogen sulfide at 25° C. for 5 hours, absorbing 9.3 lbs. $H_2S$. The mixture was washed with water, and evaporated, giving 69.4 g of light brown liquid product that analyzed C, 80.2; H, 11.8; S, 6.4; mercaptan S, 5.4. Of the total sulfur, 84% was in the form of mercaptan sulfur.

EXAMPLE 3

A mixture of 88 g (0.2 mole) of L-50 polybutene, 440 mol. wt., 50 ml. of n-pentane, and 1 ml. of trifluoromethylsulfonic acid was shaken under 25 psig hydrogen sulfide for 5.5 hours at 25° C. 9 lb. H$_2$S were absorbed. The mixture was washed with water, dried, and evaporated, giving 87.2 g of product that analyzed C, 80.9; H, 10.2; S, 4.7; mercaptan S, 3.6. Of the total sulfur, 76.6% was in the form of mercaptan sulfur.

Shorter reaction times gave lighter colored product and almost as much mercaptan content, as shown in Example 4.

EXAMPLE 4

The same mixture as in Example 2 was shaken under 25 psig hydrogen sulfide for 45 minutes, at which time 8.2 lb. H$_2$S had been absorbed. Work up as in Example 2 gave 68.7 g of light yellow product that analyzed C, 81.0; H, 12.1; S, 6.1; and mercaptan S, 5.3

Uses for the viscous polybutene mercaptans in preparing surfactants and biocides are demonstrated in these examples.

EXAMPLE 5

A mixture of 6.11 g (10 mmoles of —SH) of the mercaptan of Example 2, 10 ml. of benzene, 0.224 g (2 mmoles) of potassium tert-butylate, and 10.4 ml. (200 mmoles) of ethylene oxide was kept in a low-pressure bomb at 25° C. for 72 hours, then at 60°–70° C. for 2 hours. The mixture was cooled at 25° C., stirred in air for 1 hour to convert the potassium tert-butylate to carbonate, diluted with 20 ml. each of benzene and pentane, filtered, and evaporated. The product, 8.5 g, was a light-yellow, viscous oil, analyzing C, 64.2; H, 11.1; S, 2.55, and forming stable emulsions in water. Analysis indicates a structure of approximate composition:

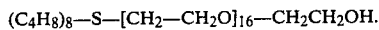

(C$_4$H$_8$)$_8$—S—[CH$_2$—CH$_2$O]$_{16}$—CH$_2$CH$_2$OH.

EXAMPLE 6

A mixture of 24.44 g (40 mmoles of mercaptan sulfur) of the product of Example 2, 150 ml. of n-heptane, 4.6 ml. (40 mmoles) of styrene, and 2. ml. of 0.1% methylene blue in acetone was shaken under 25 psig O$_2$ and illustrated with a 300 watt light bulb in a reflector at 30° C. for 96 hours, at which time it had absorbed 5.5 lbs. O$_2$. The mixture was filtered and evaporated in a Rinco evaporater at 40° C. and 0.3 torr to give 29.28 g of brown viscous oil that analyzed C, 76.9; H, 11.4; S, 5.6. Calculated for the -hydroxy-sulfoxide

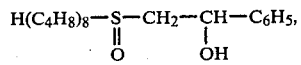

$$H(C_4H_8)_8-\underset{\underset{O}{\|}}{S}-CH_2-\underset{\underset{OH}{|}}{CH}-C_6H_5,$$

C, 77.7; H, 12.0; S, 5.2. The product had a strong absorption at 1040 cm$^{-1}$ in the infrared, typical of sulfoxides.

EXAMPLE 7

A mixture of 36.8 g (40 mmoles of mercaptan S) of the product of Example 3, L-50 mercaptan, 150 ml. of n-heptane, 4.1 ml (40 mmoles) of styrene, and 2 ml. of 0.1% methylene blue in acetone was shaken under 25 psig O$_2$ and illustrated at 30° C. for 96 hours, by which time it had absorbed 5.5 lbs. O$_2$. The mixture was filtered and evaporated, giving 42.0 g of brown, viscous oil that analyzed C, 78.8; H, 13.3; S, 4.1. It had a strong absorption at 1040 cm$^{-1}$ in the infrared, typical of sulfoxides.

The effectiveness of the novel compounds of my invention as surfactants in lowering interfacial tension between solvent-extracted 5 W oil and water was measured, using a Cenco-Du Nouy Interfacial Tensiometer #70545 with a 5 cm platinum-iridium ring at 25° C., with double-distilled water, with these results.

| Product of Example # | Concentration, % | Dynes/cm |
|---|---|---|
| — | — | 34.03 |
| 5 | 1 | 0 |
|   | 0.5 | 4 |
| 6 | 1 | 0 |
|   | 0.5 | 0 |
|   | 0.25 | 2.5 |
| 7 | 1 | 0 |
|   | 0.5 | 4.1 |

The compounds of Examples 5, 6, and 7 were tested as biocides and inhibitors for the growth of microorganisms by this test: 25 g of agar preparation were placed in standard Petri dishes. The agar preparation consisted of 23.5 g of Bacto Plate Count Agar, Difco Laboratories, Detroit, Mich., dissolved in 1 liter of water. Plate count Agar contains a standard USP formula for nutrient agar, consisting of:

| | |
|---|---|
| 5 g | Pancreatic digest of casein |
| 2.5 g | Yeast extract |
| 1 g | Glucose |
| 15 g | Agar |

Two Petri dishes were untreated and used as controls. To the others, in duplicate, were added 2.5 ml of 1% acetone solutions of the products of Examples 5, 6, and 7. All plates were uncovered for 4 hours to expose them to the spores of adventitious fungi and bacteria, then covered and stored at 30° C. for 6 days. Ratings were given at this point; 0 presents no growth, 5 shows luxuriant colonies of fungi and bacteria. Results are shown in the table.

| Product, Example # | Rating |
|---|---|
| 5 | 0,0 |
| 6 | 0,0 |
| 7 | 0,1 |
| Control | 5,5 |

The products of my invention may be used in oils or as emulsions in water of concentrations of 0.001 to 10% by weight.

I claim:

1. A process for the preparation of mercaptans which process comprises reacting olefins or polyolefins at a temperature of about −10° to 70° C. with hydrogen sulfide under pressure of about 1 to 10 atmospheres in the presence of about 0.05 to 10 percent by weight of the olefins of trifluoromethylsulfonic acid.

2. The process of claim 1 wherein the reaction temperature is about 10° to 35° C.

3. Compounds of the following formula:

$$H(C_4H_8)_h-\overset{\overset{O}{\|}}{S}-CH_2-CHOH-C_6H_5,$$

wherein h is an integer from about 6 to 10.

4. Compound of the following formula:

$$H(C_4H_8)_8-\overset{\overset{O}{\|}}{S}-CH_2CH-C_6H_5.$$

* * * * *